(12) United States Patent
Werbitzky et al.

(10) Patent No.: US 8,445,433 B2
(45) Date of Patent: May 21, 2013

(54) SYNTHESIS OF GLUCAGON-LIKE PEPTIDE

(75) Inventors: Oleg Werbitzky, Veyras (CH); Stéphane Varray, Sierre (CH); Matthieu Giraud, Sion (CH); Carsten Meininghaus, Spiez (CH)

(73) Assignee: Lonza AG, Basel (CH)

( * ) Notice: Subject to any disclaimer, the term of this patent is extended or adjusted under 35 U.S.C. 154(b) by 698 days.

(21) Appl. No.: 12/162,562

(22) PCT Filed: Jan. 11, 2007

(86) PCT No.: PCT/EP2007/000198
§ 371 (c)(1),
(2), (4) Date: Aug. 17, 2009

(87) PCT Pub. No.: WO2007/090496
PCT Pub. Date: Aug. 16, 2007

(65) Prior Publication Data
US 2009/0292106 A1    Nov. 26, 2009

(30) Foreign Application Priority Data
Feb. 8, 2006 (EP) .................................... 06002537

(51) Int. Cl.
*A61K 38/26* (2006.01)
(52) U.S. Cl.
USPC ........................................................ 514/7.2

(58) Field of Classification Search
None
See application file for complete search history.

(56) References Cited

U.S. PATENT DOCUMENTS

| 6,969,702 B2 | 11/2005 | Bertilsson et al. |
| 2008/0207507 A1 * | 8/2008 | Lau et al. ........................ 514/12 |

FOREIGN PATENT DOCUMENTS

| EP | 0164070 A1 | 12/1985 |
| EP | 0699686 A2 | 3/1996 |
| EP | 1180121 B1 | 10/2003 |
| WO | WO0155213 A2 | 8/2001 |
| WO | WO2005027978 A2 | 3/2005 |

OTHER PUBLICATIONS

Damholt et al ('Proglucagon processing profile in canine L cells expressing endogenous prohormone convertase 1/3 and prohormone convertase 2' Endocrinology v140 1999 pp. 4800-4808).*
Sampson, et al., "The synthesis of 'difficult' peptides using 2-hydroxy-4-methoxybenzyl or pseudoproline amino acid building blocks: A comparative study;" Journal of Peptide Science, vol. 5[9]: 403-409. 1999.

* cited by examiner

*Primary Examiner* — Cecilia J Tsang
*Assistant Examiner* — Ronald Niebauer
(74) *Attorney, Agent, or Firm* — Hoffmann & Baron, LLP

(57) ABSTRACT

A new method of synthesizing GLP-1 peptide is devised.

8 Claims, No Drawings

SYNTHESIS OF GLUCAGON-LIKE PEPTIDE

This application is the U.S. National Phase of, and Applicant claims priority from, International Application Number PCT/EP2007/000198 filed 11 Jan. 2007 and European Application bearing Serial No. 06002537.6 filed 8 Feb. 2006, which are incorporated herein by reference.

BACKGROUND OF THE INVENTION

The present invention relates to the field of peptide drug synthesis, namely a new method of synthesizing GLP-1 peptide agonists.

A new class of diabetic drugs, the GLP-1 or Glucagon-like peptide 1 agonists, are a promising new class of therapeutic compounds. Their preparation by standard solid-phase peptide synthesis techniques is not all that easy, though. —Basically, human GLP-1 is a naturally occurring related in sequence to Glucagon. Various, slightly modified engineered sequence variants of natural GLP-1 have been described in literature, with the aim of increasing potency.

Preparation of such GLP-1 peptides has been described in WO 05/027978 and WO 02/90388; however, no better than very basic, standard Fmoc solid phase methodology has been employed for peptide synthesis.

The applicant of the present invention found the approach of the prior art not to allow of good yields which is inacceptable for industrial manufacture. Apparently sequence dependent, individual coupling steps were found to be highly inefficient.

It is the object of the present invention to devise another or improved method of synthesizing GLP-1 peptide agonists.

This object is solved by the method of the present invention comprising comprising the use of a Fmoc-pseudoproline dipeptide unit instead of only single Fmoc-amino acids at a unique interal sequence position during solid-phase synthesis.

SUMMARY OF THE INVENTION

According to the present invention, a method of manufacturing a GLP-1 or GLP-1 agonist peptide is devised, wherein said peptide is of formula

```
                                          (SEQ ID NO: 1)
A-(R1)x-(R2)y-R3-Gly-Thr-Phe-Thr-Ser-Asp-Val-Ser-

Ser-Tyr-Leu-Glu-R8-Gln-Ala-Ala-Lys-Glu-Phe-Ile-

Ala-Trp-Leu-Val-R4-R5-(R6)w-(R7)z-B
Or is of formula
                                          (SEQ ID NO: 2)
A-(R1)x-(R2)y-R3-Gly-Thr-Phe-Thr-Ser-Asp-Val-Ser-B
Or is of formula
                                          (SEQ ID NO: 3)
A-(R1)x-(R2)y-R3-Gly-Thr-Phe-Thr-Ser-Asp-Val-Ser- Ser-B
Or is of formula
                                          (SEQ ID NO: 4)
A-(R1)x-(R2)y-R3-Gly-Thr-Phe-Thr-Ser-Asp-Val-Ser- Ser-Tyr-Leu-Glu-Gly-B
Or is of formula (SEQ ID NO: 5)
A-(R1)x-(R2)y-R3-Gly-Thr-Phe-Thr-Ser-Asp-Val-Ser- Ser-Tyr-Leu-Glu-R8-Gln-Ala-Ala-Lys-Glu-Phe-Ile- Ala-Trp-Leu-Val-R4-B
Or is of formula
                                          (SEQ ID NO: 6)
A-(R1)x-(R2)y-R3-Gly-Thr-Phe-Thr-Ser-Asp-Val-Ser- Ser-Tyr-Leu-Glu-R8-Gln-Ala-Ala-Lys-Glu-Phe-Ile- Ala-Trp-Leu-Val-R4-Gly-B
```

Wherein
B=—OH oder —NH2
A=H—, Ac—, Boc-, Fmoc-
R1=His, D-His, desamino-histidine, 2-amino-histidine, β-hydroxy-histidine, homohistidine, alpha-fluoromethyl-histidine or alpha-methyl-histidine
R2=-Ala, D-Ala, -Val, D-Val, Gly, Aib (α-aminoisobutyric acid)
R3=Glu, Asp, Met, Leu, preferably is Glu or Asp, most preferably is Asp
R4=-Lys or Arg
R5=-Gly, Aib, Ala, D-Ala
R6=Arg, Lys or Gly
R7=Arg, Lys or Gly, preferably Lys or Gly
R8=Gly or Aib And wherein, independently, x, y, w, z are 0 or 1, with the proviso that y=1 where x=1 and with the proviso that w=1 where z=1, Wherein individual amino acids may optionally carry protection groups, comprising the steps of
a. synthesizing the peptide on a solid phase by stepwise coupling of Fmoc-protected, optionally further suitably side chain protected, amino acids or dipeptides comprising pseudoproline dipeptides, in a linear fashion, with the proviso that at the unique, one suitable sequence position which reads -Val-Ser- and/or Val-Ser-Ser, respectively, and is highlighted by bold letters in the sequence formulas given above, a first pseudoproline dipeptide is coupled to the growing peptide chain which pseudoproline dipeptide is selected from the group consisting of Fmoc-Val-Ser($\psi^{Me,Me}$pro)-OH, Fmoc-Val-Ser($\psi^{H,H}$pro)-OH, Fmoc-Ser(P)-Ser($\psi^{Me,Me}$pro)-OH and Fmoc-Ser(P)-Ser($\psi^{H,H}$pro)-OH, and wherein P is an acid-cleavable side chain protection group that is cleaved under strongly acidic condition of at least 80% TFA in water, preferably P is not cleaved under weakly acidic conditions as defined below, most preferably P is tert-butyl or is trityl,
b. cleaving the peptide from the solid phase, and optionally deprotecting the peptide chain.

DETAILED DESCRIPTION OF THE INVENTION

The activity of GLP-1 peptides is highly susceptible to changes in sequence, mostly the peripheral sequence elements allowing of some conservative substitution of residues. Apparently minor changes may still then have unforeseen effects on biological stability or receptor binding and hence pharmacological activity. A good review for such is given in Sarrauste de Menthière et al, European J. Medicinal Chemistry 39, 2004:473-480. The core sequence portion of the GLP-1 peptide family does literally not allow of any change.

The linear, solid-phase synthesis of full length or partial peptides comprising this core portion encounters huge problems of individual coupling steps being utterly inefficient up to the point of near-impossibility even upon repeated coupling. Extending coupling times, raising coupling temperature etc. entail risk of increased racemisation or undesired sideproducts.

Various authors (Sarrauste, supra, and Adelhorst et al. J. Biol. Chem. 269 (1994), 6275-6278) have analyzed the secondary structure of native GLP-1-peptides in aequeous solution by circular dichroism spectroscopy (e.g. Chen et al. (1974) Determination of the helix and beta form of proteins in aqueous solution by circular dichroism. Biochemistry 13, 3350-3359, Greenfield, N. and Fasman, G. D. (1969) Computed circular dichroism spectra for the evaluation of protein conformation. Biochemistry 8, 4108-4116) and found only quite a low content (10%) of β-sheet structure causing aggregation of peptide backbones, however, aside from much larger regions of unordered and helical structure. The spectroscopic methods applied did not allow of allocating the corresponding GLP-1 sequence parts to said structural elements. —Aggregation and hence problems in solid-phase synthesis is commonly believed in the art to correlate with occurrence of extended regions of β-sheet structure. A low β-sheet structure contents is common to most peptides of at least 10 aa. length and do not correlate with any unusual problem in synthetic methodology.

Fmoc-pseudoproline dipeptide units are nowadays commercially available; their synthesis has been described (Ruckle et al., Tetrahedron 1999, 55(37): 11281-11288; Keller et al., 1998, J. Am. Chem. Soc. 120:2714-2720 for instance). Said pseudoproline peptides are used for the least for introducing at least one of the central Serine residues in the unique central sequence segment or sequence position or partial sequence -Val-Ser-Ser- allowing of using pseudoproline dipeptides for either the partial sequence -Val-Ser- or -Ser-Ser- at this sequence position, this being the gist of the present invention, and in addition to that of eventually further introducing a second pseudoproline residue in the partial sequences -Gly-Thr- or -Phe-Thr-, preferably in the partial sequence -Gly-Thr-. Said pseudoprolines of the present invention are N-Fmoc-peptidyl-(4S)-1,3-oxazolidine carboxylates derived from Ser or Thr and having in the context of the present invention the common structure of formula I

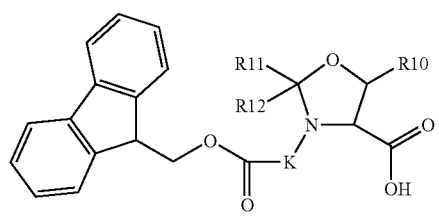

I

Wherein K is amino acid residue selected from the group consisting of Ser, Val, Phe, Gly and wherein Ser further carries a side chain-protection group P that is cleavable under strongly acidic conditions as defined below; R11,R12, independently, are H, methyl or ethyl and R10 is H or methyl. —The nature of substituents R11 and R12 influences cis/trans isomerisation of the peptide amide bond the oxazolidine is part of and hence the pseudoproline's impact of positively affecting the structure of the growing peptide chain during synthesis.

It is also feasible, but less preferred in the context of the present invention, to use pyroglutamic acids as pseudoproline moiety, requiring special coupling and deprotection chemistry (Tomasini, C. et al., Tetrahedron letters 2001, 42:5211-5214).

More preferably, only said first one pseudoproline residue at either one of the two central Ser residue sites within the GLP-1 sequence as specified above is employed in the present method of synthesis. This meaning no second pseudoproline dipeptide unit is employed during synthesis. Most preferably said first pseudoproline dipeptide is Fmoc-Val-Ser($\psi_{Me,Me}$)-OH for use in solid phase synthesis according to the present invention.

Comparative examples futily seeking to synthesize GLP-1 peptides in the absence of the unique pseudoproline dipeptide of the present invention are set forth in the experimental section, illustrating the objective technical problem that motivated the present invention.

Coupling reagents for peptide synthesis are well-known in the art (see Bodansky, M., Principles of Peptide Synthesis, $2^{nd}$ ed. Springer Verlag Berlin/Heidelberg, 1993; also see discussion of role of coupling additives or auxilliaries therein). Coupling reagents may be mixed anhydrides (e.g. T3P: propane phosphonic acid anhydride) or other acylating agents such as activated esters or acid halogenides (e.g. ICBF, isobutyl-chloroformiate), or they may be carbodiimides (e.g. 1-ethyl-3-(3-dimethylaminopropyl)-carbodiimide, diisopropyl-carbodiimide), activated benzotriazine-derivatives (DEPBT: 3-(diethoxyphosphoryloxy)-1,2,3-benzotriazine-4 (3H)-one) or uronium or phosphonium salt derivatives of benzotriazol.

In view of best yield, short reaction time and protection against racemization during chaing elongation, more preferred is that the coupling reagent is selected from the group consisting of uronium salts and phosphonium salts of the benzotriazol capable of activating a free carboxylic acid function along with that the reaction is carried out in the presence of a base. Suitable and likewise preferred examples of such uronium or phosphonium coupling salts are e.g. HBTU (O-1H-benzotriazole-1-yl)-N,N,N',N'-tetramethyluronium hexafluorophosphate), BOP (benzotriazole-1-yl-oxy-tris-(dimethylamino)-phosphonium hexafluorophosphate), PyBOP (Benzotriazole-1-yl-oxy-tripyrrolidinophosphonium hexafluorophosphate), PyAOP, HCTU (O-(1H-6-chloro-benzotriazole-1-yl)-1,1,3,3-tetramethyluronium hexafluorophosphate), TCTU (O-1H-6-chlorobenzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TOTU (O-[cyano(ethoxycarbonyl)methyleneamino]-N,N,N',N"-tetramethyluronium tetrafluoroborate), HAPyU (O-(benzotriazol-1-yl)oxybis-(pyrrolidino)-uronium hexafluorophosphate.

Preferably, the base reagent is a weak base whose conjugated acid has a pKa value of from pKa 7.5 to 15, more preferably of from pKa 7.5 to 10, with the exclusion of an α-amino function of a peptide or amino acid or amino acid derivative, and which base preferably is a tertiary, sterically hindered amine. Examples of such and further preferred are Hünig-base (N,N-diisopropylethylamine), N,N'-dialkylaniline, 2,4,6-trialkylpyridine, 2,6-trialkylpyridine or N-alkylmorpholine with the alkyl being straight or branched C1-C4 alkyl, more preferably it is N-methylmorpholine (NMM) or collidine (2,4,6-trimethylpyridine), most preferably it is collidine.

The use of coupling additives, in particular of coupling additives of the benzotriazol type, is also known (see Bodansky, supra). Their use is particularly preferred when using the highly activating, afore said uronium or phosphonium salt coupling reagents. Hence it is further preferred that the coupling reagent additive is a nucleophilic hydroxy compound capable of forming activated esters, more preferably having an acidic, nucleophilic N-hydroxy function wherein N is imide or is N-acyl or N-aryl substituted triazeno, most preferably the coupling additive is a N-hydroxy-benzotriazol derivative (or 1-hydroxy-benzotriazol derivative) or is an N-hydroxy-benzotriazine derivative. Such coupling additive N-hydroxy compounds have been described in large and wide in WO 94/07910 and EP-410 182 and whose respective disclosure is incorporated by reference hereto. Examples are e.g. N-hydroxy-succinimide, N-hydroxy-3,4-dihydro-4-oxo-1,2,3-benzotriazine (HOOBt), 1-hydroxy-7-azabenzotriazole (HOAt) and N-hydroxy-benzotriazole (HOBt). N-hydroxy-benzotriazine derivatives are particularly preferred, in a most preferred embodiment, the coupling reagent additive is hydroxy-3,4-dihydro-4-oxo-1,2,3-benzotriazine.

Ammonium salt compounds of coupling additives are known and their use in coupling chemistry has been described, for instance in U.S. Pat. No. 4,806,641.

It is also possible to employ, concomittant with its role as a coupling auxilliary, e.g. HOBt as a ion-pairing reagent for protection of Arg side chains during synthesis, as an option to covalent side chain protection of Arg. In that case, a sufficiently high concentration of HOBt must be maintained through out all cyclical processing steps of solid phase synthesis.

In a further particularly preferred embodiment, the uronium or phosphonium salt coupling reagent is an uronium salt reagent and preferably is HCTU, TCTU or HBTU and even more preferably is used in the reaction in combination with N-hydroxy-3,4-dihydro-4-oxo-1,2,3-benzotriazine or a salt thereof. This embodiment is mainly preferred for use in chain elongation step of peptide synthesis after removal of the base-labile Nα-protection group, but may as well be used for lactamization reaction during side-chain cyclization.

In the context of the present invention, it is to be noted that HCTU and TCTU are defined as to be encompassed by the term 'uronium salt reagent' as commonly understood in the art despite that these compounds and possible analogues have been shown to comprise an isonitroso moiety rather than an uronium moiety by means of crystal structure analysis (O. Marder, Y. Shvo, and F. Albericio "*HCTU and TCTU: New Coupling Reagents: Development and Industrial Applications*", Chimica Oggi 2002, 20:37-41), an N-amidino substituent on the heterocyclic core giving rise to a guanidium structure instead. In the present context, such class of compounds is termed 'guanidium-type subclass' of uronium salt reagents according to the present invention.

Deprotection of the base labile Nα may be carried out as routinely done in the art, e.g. with 20% piperidine in N-methyl morpholine (NMP), dichloromethane (DCM) or dimethylformamide (DMF). Both organic apolar aprotic solvents solvents are routinely applied in the art for all steps of solid-phase synthesis. NMP is a preferred solvent.

Fmoc amino acids or dipeptides are preferably coupled with normal 1-3 eq., more preferably with only 1-2 eq. of such Fmoc amino acid reagent per eq. of reactive, solid-phase bound amino function as determinable e.g. by Kaiser Test. The coupling temperature is usually in the range of from 15 to 30° C., especially where using phosphonium or uronium type coupling reagents. Typically, a temperature of about 20 to 25° C. is applied for coupling.—It is an advantage of the method of the present invention having devised a method of synthesis allowing of high yield of product or excellent purity of GLP-1 product without being forced to use precious, biohazardous reagents in excessive amount, essentially wasting most of that excess in the reaction's effluents.

Protections groups and their use, mainly for protection of amino acid side chains or Nα-terminal amino groups, are well known in the art (cp. Bodanzsky, supra). Commonly employed carboxy-protection groups for Glu, Asp are e.g. Mpe, O-1-Adamantyl, O-benzyl and even simply alkyl esters may be used, though less commonly used. For sake of ease, typically and preferably tert.butyl groups are used. -Tyrosin may be protected by different protection groups, e.g. tert.butyl ether or Z- or more preferably 2-Bromo-Z esters. It is equally possible to use tritylalkohol protection groups such as 2-chloro-trityl or 4-methoxy or 4,4' methoxy-trityl groups. Preferably, it is a trityl or a tert.butyl protection group. More preferably, it is a tertiary butyl (tBu) protection group, meaning the tyrosyl side chain is modified to a tertiary-butyl ether. The tBu group is only efficiently removed under strongly acidic condition. -Arginine protection group may be preferably selected from the group consisting of 2,2,4,6,7-pentamethyldihydrobenzofuranyl-5-sulfonyl (Pbf), adamantyloxycarbonyl and isobornyl-oxy-carbonyl, 2,2,5,7,8-pentamethylenchromanesulfonyl-6-sulfonyl (Pmc), 4-methoxy-2,3,6-trimethylbenzenesulfonyl (Mtr) and its 4-tert.butyl-2,3,5,6-tetramethyl homologue (Tart) or Boc, which are only cleaved under strongly acidic conditions as defined above. More preferably, it is Pbf, Pmc, Mtr, most preferably, it is Pbf; upon global deprotection of side chains under strongly acidic conditions, in usually aequeous medium, bystander-alkylation of deprotected tyrosine is not observed with Pmc,Mtr and esp. Pbf. Pbf's cleavage rate is the hightest ever.—Note the hint to optional ion-pairing protection mode with HOBt.—Ser, Thr typically may be typically and preferably protected by e.g. tert.-butyl or trityl, most preferably tert-butyl. Other modes of protection are equally feasible, e.g. with benzyl, though less preferred since eventually requiring hydrogenolytic removal or extended incubation at strongly acidic incubation, which is both equally undesirable. Similar considerations apply to protection of Lys or Nor- or Homo-lysine; typically and preferably, Lys is protected with Boc. -Trp must no necessarily protected during solid-phase synthesis, though protection with typically Boc is preferred.—As regards side chain protection groups, the afore said is valid both for the natural L-amind acids as well as for their D-homologues.

The solid phase S is to be understood as to amount to a solid, non-soluble support material, such controlled pore size glass, silica or more commonly a polymeric organic resin such as for instance the classical polystyrene-divinylbenzene resin (PS resin) used by Merrifield along with hydroxybenzyl-phenyl integral linker moieties for attaching peptide thereto or PS resin used by Wang with hydroxy-benzyl-p-benzyloxy moieties directly linked to the resin. Such functional sites for attachment of peptide are termed linker in the present context, and are understood to be tacidly inferred as a mandatory feature by the term 'solid-phase' in the present context. If need be, other linker moieties such as e.g. more specialized, for instance more acid-labile, linkers may be further grafted to the said first, integral linkers on the premade solid phase and is often then referred to as a 'handle' in the art. Further examples of such are linker- or handle-resin composites are (4-methoxyphenyl)-aminomethyl- or -hydroxymethyl and (4-methylphenyl)-aminomethyl- or -hydroxymethyl-PS solid phases (Atkinson et al., 2000, J. Org. Chem. 65, 5048) in O or N-linkage to the peptide moiety, respectively, allowing both of genertion of C-terminal acid or carboxamide group upon final cleavage of peptide from resin.

For the purposes of the present invention, a solid phase resin, for use in synthesis, mandatorily comprises at least one integral linker or handle which is part of the solid phase core material; such linker or handle may be considered as an immobilized protection group (Guillier et al, Chem. Rev. 100, 2091-2157, 2000). Typically, a given solid phase comprising an inert solid support or resin is addressed by virtue of the chemical nature of its linker of handle group allowing of acylation with amino acid or peptide.

More complex PEG-grafted polystyrene resins such as tentagel-based Novasyn TG (Novabiochem, Merck Biosciences, Germany) which are available with different grafted handles or linkers are more amphilic than standard PS resin, and also impact synthetic efficiency. In the context of the present invention, use of a solid phase made up from a linker or handle moiety and a PS resin that is devoid of PEG or other polyoxyalkylene segments is preferred. Integral or grafted PEG or polyoxyalkylene resins and hence solid phase are less preferred and are preferably disclaimed by the present invention.

Resins as used in the present invention are of standard mesh size (US bureau of standards), which is about 50-500 mesh, more preferably 100 to 400 mesh.

It is possible to use photocleavable linkers such as for instance a carboxamide generating, photocleavable linker described in Holmes et al., 1995, J. Org. Chem. 60, 2318). In another preferred embodiment, the solid phases of the present invention allows of cleavage of peptide from a solid phase under strongly acidic conditions. By definition, according to the present invention, a strongly acidic condition as being opposed to a weakly acidic condition means applying at least 50% (v/v) trifluoro acetic acid (TFA) in the solvent. Further, conversely, a protection group requiring strongly acidic condition for removal is a protection group that can be removed, at the very least, by 80% TFA. Accordingly, protection groups that require even stronger acids such as HF do not come under the afore mentioned definition in the context of the present invention.

A weakly acidic condition is defined by having 0.01% (v/v) to <50% TFA, preferably having 0.1% to 30% TFA. The term 'acid-labile' refers to essentially quantitative cleavage in 2-10% TFA in dichloromethane at ambient temperature for at least an hour.

In the specific context of the present invention, the above specified GLP-1 peptides cleaved from the solid phase and having been mostly or completely deprotected are giving foamy, geleous solutions with mostly commonly employed solvents or solvents mixtures. Handling such gelous solution easily results in considerable losses of material, in particular along with filtration operations for separation from solid phase. In a preferred embodiment, the solid phase is a solid phase that is cleavable from then still protected peptide under weakly acidic conditions as defined above, using an acid-labile solid phase. In such mode, firstly the peptide is cleaved from the solid phase and is then, in a second step, side chain deprotected under strongly acidic conditions as defined above.

In one further preferred embodiment, the GLP-1 peptides is set free from the resin as a C-termainal carboxamide. Examples of such Carboxamide generating resins are e.g. PAL resin (5-(4-amino-methyl-3,5-dihydroxyphenoxy) valeric acid ester), Sieber resin (Sieber, P. 1987, Tetrahedron Lett. 28, 2107) or related xanthenylamide type resins (e.g. U.S. Pat. No. 5,306,562), Rink amide resin (Rink, H. 1987, Tetrahedron Lett. 28:3787), BAL resin (4-(4-formyl-3,5-dimethoxyphenoxy)-butyric acid ester, Tetrahedron Lett. 43:3543), preferably an acid-labile Carboxymide generating resin is used such as e.g. Sieber resin or other xantenylamide type resin or BAL resin which are also the most preferred embodiments.

In another preferred embodiment, the solid phase is an acid-labile solid phase which is liberating a C-terminal carboxylic acid upon cleavage of the protected peptide from the solid phase. Both examples and further preferred embodiments of such are 2'-chloro-trityl, 4-methoxy or 4,4'-dimethoxy-trityl, 4-methyltrityl resins or related, but different 2-(4-hydroxy-phenyl)-2,2-diphenyl-acetyl resin derivable from an amino- or hydroxy functionalized resin by acylation with Bayer's 4-carboxytrityl linker, and sold for instance under the brand of Novasyn TG resin. Further examples are e.g. acid-labile Rink acid resin (4-(2',4'-dimethoxyphenyl-hydroxymethyl)phenoxy, Rink et al., 1987, Tetrahedron Lett. 28, 3787) and HMPB-resin (Sieber et al., 1987, Tetrahedron Lett. 28, 6147; HMPB: 4-hydroxymethyl-3-methoxyphenoxybutyryl, usually coupled as a secondary handle to a rink amide resin or a derivative thereof.

Most preferably, the peptide according to the present invention is carboxyterminally coupled to the resin or resin handle (S=solid phase or resin optionally resin with handle).

Further preferred are particular peptide sequences and respective peptide-solid phase conjugates as listed below, alone or in combination with the above further preferred embodiments:

```
                                            (SEQ. ID. No. 7)
1. A-His-Ala-Glu-Gly-Thr-Phe-Thr-Ser-Asp-Val-Ser-

Ser-Tyr-Leu-Glu-Gly-Gln-Ala-Ala-Lys-Glu-Phe-

Ile-Ala-Trp-Leu-Val-Lys-Gly-Arg-S
   or
                                            (SEQ ID NO: 7)
   A-His-Ala-Glu-Gly-Thr-Phe-Thr-Ser-Asp-Val-

Ser-Ser-Tyr-Leu-Glu-Gly-Gln-Ala-Ala-Lys-

PGlu-he-Ile-Ala-Trp-Leu-Val-Lys-Gly-Arg-NH2
                                            (SEQ ID NO: 8)
2. A-His-Ala-Glu-Gly-Thr-Phe-Thr-Ser-Asp-Val-Ser-

Ser-Tyr-Leu-Glu-Gly-Gln-Ala-Ala-Lys-Glu-Phe-

Ile-Ala-Trp-Leu-Val-Arg-Gly-Arg-Gly-S
   or
                                            (SEQ ID NO: 8)
   A-His-Ala-Glu-Gly-Thr-Phe-Thr-Ser-Asp-Val-Ser-

Ser-Tyr-Leu-Glu-Gly-Gln-Ala-Ala-Lys-Glu-Phe-

Ile-Ala-Trp-Leu-Val-Arg-Gly-Arg-Gly-OH or -NH2

3. A-His-D-Ala-Glu-Gly-Thr-Phe-Thr-Ser-Asp-Val-

Ser-Ser-Tyr-Leu-Glu-Gly-Gln-Ala-Ala-Lys-Glu-

Phe-Ile-Ala-Trp-Leu-Val-Lys-Gly-Gly-S or A-His-

D-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-

Ala-Trp-Leu-Val-Lys-Gly-Gly-OH or -NH2

4. A-D-Ala-Glu-Gly-Thr-Phe-Thr-Ser-Asp-Val-Ser-

Ser-Tyr-Leu-Glu-Gly-Gln-Ala-Ala-Lys-Glu-Phe-

Ile-Ala-Trp-Leu-Val-Lys-Gly-Arg-Lys-S or A-D-
```

-continued

```
Ala-Glu-Gly-Thr-Phe-Thr-Ser-Asp-Val-Ser-Ser-

Tyr-Leu-Glu-Gly-Gln-Ala-Ala-Lys-Glu-Phe-Ile-

Ala-Trp-Leu-Val-Lys-Gly-Arg-Lys-NH₂

(SEQ ID NO: 9)
5. A-Glu-Gly-Thr-Phe-Thr-Ser-Asp-Val-Ser-Ser-Tyr-

Leu-Glu-Gly-Gln-Ala-Ala-Lys-Glu-Phe-Ile-Ala-

Trp-Leu-Val-Lys-NorVal-Arg-S
or
                                       (SEQ ID NO: 9)
A-Glu-Gly-Thr-Phe-Thr-Ser-Asp-Val-Ser-Ser-Tyr-

Leu-Glu-Gly-Gln-Ala-Ala-Lys-Glu-Phe-Ile-Ala-Trp-

Leu-Val-Lys-NorVal-Arg-NH₂ with NorVal being

Nor-L-valine which is α-aminoisobutyric acid or α-methylalanine, commonly referred to by the acronym -Aib for short.
```

INCORPORATION OF SEQUENCE LISTING

Incorporated herein by reference in its entirety is the Sequence Listing for the application. The Sequence Listing is disclosed on a computer-readable ASCII text file titled, "Sub_Sequence_1686-112PCT_US.txt", created on May 21, 2012. The "Sub_Sequence_1686-112_PCT_US.txt" file is 6.0 kb in size.

EXPERIMENTS

Example 1

Synthesis of H-His-Ala-Glu-Gly-Thr-Phe-Thr-Ser-Asp-Val-Ser-Ser-Tyr-Leu-Glu-Gly-Gln-Ala-Ala-Lys-Glu-Phelle-Ala-Trp-Leu-Val-Arg-Gly-Arg-Gly-OH (SEQ ID NO: 8) employing Fmoc-Val-Ser($\psi^{Me,Me}$-pro)-OH The above peptide was obtained by linear Fmoc synthesis. All amino acids coupled were commercially available Fmoc-monoamino acids, except for one coupling step where the pseudoproline dipeptide Fmoc-Val-Ser($\psi^{Me,Me}$pro)-OH (obtained from Merck Biosciences GmbH, Schwalbach/Germany, Novabiochem brand products) was coupled to the N-terminal sequence Ser-Tyr-Leu-Glu- (SEQ ID NO: 10) in the course of synthesis. Further exception, the last His residue was coupled as a Boc-His residue; no protection was conferred to His-side chain. Side chain protection groups employed; for ease of listing, the use of N-terminal Fmoc protection is not further mentioned: Arg(Pbf), Asp(tbu), Gln (Trt), Glu(tbu), Lys(Boc), Ser(tbu), Thr(tbu), Trp(Boc), Tyr (tbu).

Synthesis at 3 mmol scale started on a Fmoc-Gly-2-chlorotrityl polystyrene resin (i.e. 2-CTC resin preloaded with Fmoc-glycine, order number RAA-1039, Loading: >0.5 mmol/mL, 100-200 Mesh, obtained from CBL-Patras, Greece). Initially, resin was swelled with dichloromethane. Standard Fmoc Synthesis using 2 to 2.5 eq. of Fmoc amino acids for coupling, employing HBTU activation of amino acids at 25° C. for 30 min. in the presence of diisopropylamine/HOBt in dichloromethane-N-methylmorpholine (DCM:NMP=1:3) solvent system. No preactivation was carried out but all reagents were simply mixed in a single step. Fmoc deprotection was achieved by 20% (w/w) piperidine in NMP followed by NMP washes to completely remove the base reagent. Washing efficiency was assessed by chloranil test; washing was repeated until no blue colouring could be observed any more prior to coupling. All couplings proceeded well and did not require re-coupling, except for the terminal Boc-His, probably due to solubility problem in DCM which might be diminished by adding minor amount of DMSO as a co-solvent. Coupling efficiency could be moderately further improved by using non-side chain protected Fmoc-Gln instead of Fmoc-Gln(Trt) for position Gln-17.

In a first step, the still Boc protected peptide was cleaved from resin in 2% TFA in DCM at 0° C. for at least 10-30 min; three repeated TFA cycles of 15. min was shown to work best, each one followed by pyridine treatment and rinsing. 1% (w/w) triethylsilane (TES) was used as scavenger. The reaction was stirred by nitrogen bubbling. After cleavage, TFA was neutralized using pyridine by pouring the reaction broth into dilute pyridine (pyridine/ethanol 1:9 (v/v). Resin is rinsed with DCM and the solvent stripped off by filtration. A solvent exchange of the filtrate from DCM to ethanol was done by distilling off the DCM under vacuo, and finally the protected peptide was precipitated by addition of water and filtrated. The cake was washed three times with water and the peptide was dried under vacuo at RT. At this stage, material with a purity of about 77.3% area (as assessed by HPLC) amounting to a 77% yield was obtained. The molecular mass observed with HPLC-MS corresponded to the theoretically expected mass. Solubility of this product in standard solvent such as DCM was perfect.

In a second step, global deprotection was carried out in DCM diluted with cleavage cocktail ('CC'), DCM: 'CC'=1: 10 (v/v). For the GLP-1 peptide, rather than pure DCM, addition of of 0.1 up to 1 part of trifluoroethanol per part pure DCM was found optimal for optimizing solubility of peptide during deprotection. 'CC' was made up of TFA/thioanisole/phenol/water/TES in the mixing ratio (% w/w): 89:2.5:2.5: 5.0:1.0.—The dry product from the preceding cleavage step was dissolved in 10 ml DCM diluted as said above with 'CC' and stirred for 5 hours at room temperature. The product was then recovered by addition of 50 ml methyl-tert.butyl-ether (MTBE, Fluka Chemie, Buchs/Switzerland), cooling the reaction down to 0° C. in a water bath for 30 min. under stirring and filtrating off the salt precipitate that had formed in the whiletime. The filter cake is rinsed with MTBE several times which is then dried at room temperature, yielding 0.8 g of a crude product of about 95% purity as determined by HPLC. The total yield jointly over steps 2 and 3 was about 75%.

Example 2

Comparative Example synthesis of N-terminal fragment H-His-Ala-Glu-Gly-Thr-Phe-Thr-Ser-Asp-Val-Ser-Ser-Tyr-Leu-Glu-Gly-OH (SEQ ID NO: 10) (fragment 1 to 11) in the absence pseudoproline Initially, solid phase synthesis of said small fragment was carried out essentially as described in example 1, except that a shorter fragment only was set out to be synthesized. Using 2.5 to 3 eq. of amino acid for each coupling reaction, the amino acids 15 to 9 were all coupled with ease. However, the following Fmoc amino acids 8 to 1 posed severe problems: Only at two positions, coupling proceded with similiar ease. All other positions required at least two repeated cycles of coupling but still did not allow of satisfactory yields of more than 30% purity.—In order to assess the severity of the problem, and disregarding commonly known aspect of undue racemization, a sheer force coupling approach used 4. eq. of amino acid, increased the temperature for at least the coupling of the commonly less racemisation prone amino acids to 30 to 40° C. and used more active 6-Cl-HOBt instead. However, still then steady re-couplings were required and no significant improvement of coupling efficiency per se could be observed.—Cleavage from resin proceeded in a first step as described in example 1 in 2% TFA, except that the fragment proved to have very unique solubility behaviour. The protected, uncleaved fragment formed a gelt after addition of pyridine. Consequently pyridine needed to be added after the filtration step to the filtrate only; the DCM distillation was found to be very difficult as the gel was foaming, leaving solid everywhere and reducing yield drastically. Upon addition of water, a solid formed that could be isolated. However, solubilizing said solid product thereafter again proved difficult: The protected fragment is largely insoluble in DCM, THF, acetonitrile and mixtures thereof. Addition of LiCl in THF did not improve solubility. —The peptide proved to be slightly solube in NMP, DMF or DMSO, giving a gel-like appearance at more reasonable concentrations, and hence mandating to work in highly dilute solution which was found suboptimal for yield.

The invention claimed is:

1. A solid phase conjugated GLP-1 or GLP-1 agonist peptide, wherein said peptide is of formula SEQ ID NO: 1
A-(R1)x-(R2)y-R3-Gly-Thr-Phe-Thr-Ser-Asp-Val-Ser-Ser-Tyr-Leu-Glu-R8-Gln-Ala-Ala-Lys-Glu-Phe-Ile-Ala-Trp-Leu-Val-R4-R5-(R6)w-(R7)z-S or is of formula SEQ ID NO: 3
A-(R1)x-(R2)y-R3-Gly-Thr-Phe-Thr-Ser-Asp-Val-Ser-Ser-S or is of formula SEQ ID NO: 4
A-(R1)x-(R2)y-R3-Gly-Thr-Phe-Thr-Ser-Asp-Val-Ser-Ser-Tyr-Leu-Glu-Gly-S or is of formula SEQ ID NO: 5
A-(R1)x-(R2)y-R3-Gly-Thr-Phe-Thr-Ser-Asp-Val-Ser-Ser-Tyr-Leu-Glu-R8-Gln-Ala-Ala-Lys-Glu-Phe-Ile-Ala-Trp-Leu-Val-R4-S or is of formula SEQ ID NO: 6
A-(R1)x-(R2)y-R3-Gly-Thr-Phe-Thr-Ser-Asp-Val-Ser-Ser-Tyr-Leu-Glu-R8-Gln-Ala-Ala-Lys-Glu-Phe-Ile-Ala-Trp-Leu-Val-R4-Gly-S wherein S=solid phase bonded C-terminally covalently to the peptidyl moiety via thioester, ester or amido group or optionally covalently via, where the C-terminal amino acid is a lysine, the ε-amino function of said lysine;

A=H-, Ac-, Boc-, Fmoc-;

R1=His, D-His, desamino-histidine, 2-amino-histidine, β-hydroxy-histidine, homohistidine, alpha-fluoromethyl-histidine or alpha-methyl-histidine;

R2=Ala, D-Ala, Val, D-Val, Gly, Aib (α-aminoisobutyric acid);
R3=Glu, Asp, Met, Leu;
R4=-Lys or Arg;
R5=-Gly, Aib, Ala, D-Ala;
R6=Arg, Lys or Gly;
R7=Arg, Lys or Gly;
R8=Gly or Aib;
and wherein, independently, x, y, w, z are 0 or 1, with the proviso that y=1 where x=1 and with the proviso that w=1 where z=1, wherein individual side chains of at least Lys, Thr, Ser, Glu, Asp carry non-base labile protection groups which protection groups may be pseudoproline protection groups which form pseudoproline protected residues in case of Thr or Ser and wherein a first pseudoproline protected residue is located in the unique sequence segment -Val-Ser-Ser and is a pseudoproline-oxazolidine derivative of Serine.

2. A solid phase conjugated peptide according to claim 1, wherein R3 is Glu or Asp.

3. A solid phase conjugated peptide according to claim 1, wherein R7 is Lys or Gly.

4. A solid phase conjugated peptide according to claim 1, wherein said protection groups are acid cleavable.

5. A solid phase conjugated peptide according to claim 1, characterized the peptide comprises at least one second pseudoproline protected residue which is -Thr($\psi^{Me,Me}$pro)- or is Thr($\psi^{H,H}$pro)- and is located in the unique sequence segment-Gly-Thr-.

6. A solid phase conjugated peptide according to claim 5, wherein the peptide comprises only two pseudoproline-protected residues which are said first and second pseudoproline residues.

7. A solid phase conjugated peptide according to claim 1, wherein the pseudoproline-oxazolidine derivative of Serine is selected from the group consisting of -Ser($\psi^{Me,Me}$pro)- or -Ser($\psi^{H,H}$pro).

8. A solid phase conjugated peptide according to claim 7, characterized in that said Ser($\psi$-pro)-pseudoproline is the only pseudoproline-protected residue in the peptide.

* * * * *

UNITED STATES PATENT AND TRADEMARK OFFICE
CERTIFICATE OF CORRECTION

| | | |
|---|---|---|
| PATENT NO. | : 8,445,433 B2 | |
| APPLICATION NO. | : 12/162562 | |
| DATED | : May 21, 2013 | |
| INVENTOR(S) | : Werbitzky et al. | |

It is certified that error appears in the above-identified patent and that said Letters Patent is hereby corrected as shown below:

IN THE CLAIMS:

Claim 5, column 20, line 6:

Now reads:   "characterized the peptide"

Should read:   -- wherein the peptide --

Claim 8, column 20, line 19:

Now reads:   "characterized in that"

Should read:   -- wherein --

Signed and Sealed this
Seventeenth Day of September, 2013

Teresa Stanek Rea
*Deputy Director of the United States Patent and Trademark Office*

SEQUENCE LISTING

```
<160> NUMBER OF SEQ ID NOS: 11

<210> SEQ ID NO 1
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be His or may be absent.
<220> FEATURE:
<221> NAME/KEY: MISC_FEATURE
<222> LOCATION: (2)..(2)
<223> OTHER INFORMATION: Xaa can be Ala, Val, Gly, or may be absent.
<220> FEATURE:
<221> NAME/KEY: MISC_FEATURE
<222> LOCATION: (3)..(3)
<223> OTHER INFORMATION: Xaa can be Glu, Asp, Met, or Leu.
<220> FEATURE:
<221> NAME/KEY: MISC_FEATURE
<222> LOCATION: (16)..(16)
<223> OTHER INFORMATION: Xaa can be Gly or may be absent.
<220> FEATURE:
<221> NAME/KEY: MISC_FEATURE
<222> LOCATION: (28)..(28)
<223> OTHER INFORMATION: Xaa can be Lys or Arg.
<220> FEATURE:
<221> NAME/KEY: MISC_FEATURE
<222> LOCATION: (29)..(29)
<223> OTHER INFORMATION: Xaa can be Gly or Ala or may be absent.
<220> FEATURE:
<221> NAME/KEY: MISC_FEATURE
<222> LOCATION: (30)..(30)
<223> OTHER INFORMATION: Xaa can be Arg, Lys or Gly.
<220> FEATURE:
<221> NAME/KEY: MISC_FEATURE
<222> LOCATION: (31)..(31)
<223> OTHER INFORMATION: Xaa can be Arg, Lys or Gly.

<400> SEQUENCE: 1

Xaa Xaa Xaa Gly Thr Phe Thr Ser Asp Val Ser Ser Tyr Leu Glu Xaa
1               5                   10                  15

Gln Ala Ala Lys Glu Phe Ile Ala Trp Leu Val Xaa Xaa Xaa Xaa
            20                  25                  30

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be His or may be absent.
<220> FEATURE:
<221> NAME/KEY: MISC_FEATURE
<222> LOCATION: (2)..(2)
```

```
<223> OTHER INFORMATION: Xaa can be Ala, Val, Gly, or may be absent.
<220> FEATURE:
<221> NAME/KEY: MISC_FEATURE
<222> LOCATION: (3)..(3)
<223> OTHER INFORMATION: Xaa can be Glu, Asp, Met, or Leu.

<400> SEQUENCE: 2

Xaa Xaa Xaa Gly Thr Phe Thr Ser Asp Val Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be His or may be absent.
<220> FEATURE:
<221> NAME/KEY: MISC_FEATURE
<222> LOCATION: (2)..(2)
<223> OTHER INFORMATION: Xaa can be Ala, Val, Gly, or may be absent.
<220> FEATURE:
<221> NAME/KEY: MISC_FEATURE
<222> LOCATION: (3)..(3)
<223> OTHER INFORMATION: Xaa can be Glu, Asp, Met, or Leu.

<400> SEQUENCE: 3

Xaa Xaa Xaa Gly Thr Phe Thr Ser Asp Val Ser Ser
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be His or may be absent.
<220> FEATURE:
<221> NAME/KEY: MISC_FEATURE
<222> LOCATION: (2)..(2)
<223> OTHER INFORMATION: Xaa can be Ala, Val, Gly, or may be absent.
<220> FEATURE:
<221> NAME/KEY: MISC_FEATURE
<222> LOCATION: (3)..(3)
<223> OTHER INFORMATION: Xaa can be Glu, Asp, Met, or Leu.

<400> SEQUENCE: 4

Xaa Xaa Xaa Gly Thr Phe Thr Ser Asp Val Ser Ser Tyr Leu Glu Gly
1               5                   10                  15

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be His or may be absent.
<220> FEATURE:
<221> NAME/KEY: MISC_FEATURE
<222> LOCATION: (2)..(2)
<223> OTHER INFORMATION: Xaa can be Ala, Val, Gly, or may be absent.
<220> FEATURE:
<221> NAME/KEY: MISC_FEATURE
<222> LOCATION: (3)..(3)
<223> OTHER INFORMATION: Xaa can be Glu, Asp, Met, or Leu.
```

```
<220> FEATURE:
<221> NAME/KEY: MISC_FEATURE
<222> LOCATION: (16)..(16)
<223> OTHER INFORMATION: Xaa can be Gly or may be absent.
<220> FEATURE:
<221> NAME/KEY: MISC_FEATURE
<222> LOCATION: (28)..(28)
<223> OTHER INFORMATION: Xaa can be Lys or Arg.

<400> SEQUENCE: 5

Xaa Xaa Xaa Gly Thr Phe Thr Ser Asp Val Ser Ser Tyr Leu Glu Xaa
1               5                   10                  15

Gln Ala Ala Lys Glu Phe Ile Ala Trp Leu Val Xaa
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be His or may be absent.
<220> FEATURE:
<221> NAME/KEY: MISC_FEATURE
<222> LOCATION: (2)..(2)
<223> OTHER INFORMATION: Xaa can be Ala, Val, Gly, or may be absent.
<220> FEATURE:
<221> NAME/KEY: MISC_FEATURE
<222> LOCATION: (3)..(3)
<223> OTHER INFORMATION: Xaa can be Glu, Asp, Met, or Leu.
<220> FEATURE:
<221> NAME/KEY: MISC_FEATURE
<222> LOCATION: (16)..(16)
<223> OTHER INFORMATION: Xaa can be Gly or may be absent.
<220> FEATURE:
<221> NAME/KEY: MISC_FEATURE
<222> LOCATION: (28)..(28)
<223> OTHER INFORMATION: Xaa can be Lys or Arg.

<400> SEQUENCE: 6

Xaa Xaa Xaa Gly Thr Phe Thr Ser Asp Val Ser Ser Tyr Leu Glu Xaa
1               5                   10                  15

Gln Ala Ala Lys Glu Phe Ile Ala Trp Leu Val Xaa Gly
            20                  25

<210> SEQ ID NO 7
<211> LENGTH: 30
<212> TYPE: PRT
<213> ORGANISM: Artificial Sequence
<220> FEATURE:
<223> OTHER INFORMATION: Synthetic peptide

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic peptide

<400> SEQUENCE: 8

His Ala Glu Gly Thr Phe Thr Ser Asp Val Ser Ser Tyr Leu Glu Gly
```

```
                    1               5                  10                  15

Gln Ala Ala Lys Glu Phe Ile Ala Trp Leu Val Arg Gly Arg Gly
                    20                  25                  30

<210> SEQ ID NO 9
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: Aib
<222> LOCATION: (27)..(27)
<223> OTHER INFORMATION: Aib

<400> SEQUENCE: 9

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Val Arg
                20                  25

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Ser Tyr Leu Glu
1

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

His Ala Glu Gly Thr Phe Thr Ser Asp Val Ser Ser Tyr Leu Glu Gly
1               5                   10                  15
```